United States Patent
McCausland

(10) Patent No.: US 7,183,378 B2
(45) Date of Patent: Feb. 27, 2007

(54) PROTEIN PRODUCTION

(75) Inventor: Linda Jane McCausland, West Lafayette, IN (US)

(73) Assignee: Accentus PLC, London (GB)

( * ) Notice: Subject to any disclaimer, the term of this patent is extended or adjusted under 35 U.S.C. 154(b) by 0 days.

(21) Appl. No.: 10/528,406

(22) PCT Filed: Aug. 14, 2003

(86) PCT No.: PCT/GB03/03550

§ 371 (c)(1),
(2), (4) Date: Oct. 12, 2005

(87) PCT Pub. No.: WO2004/026340

PCT Pub. Date: Apr. 1, 2004

(65) Prior Publication Data

US 2006/0052583 A1    Mar. 9, 2006

(30) Foreign Application Priority Data

Dec. 21, 2002 (GB) ................. 0229967.5

(51) Int. Cl.
*C07K 1/00* (2006.01)
(52) U.S. Cl. .................................... 530/350
(58) Field of Classification Search .................... None
See application file for complete search history.

(56) References Cited

U.S. PATENT DOCUMENTS 4,661,350 A    4/1987    Tsurumizu ................. 424/92
4,792,331 A    12/1988   Philippot .................. 604/187
6,060,293 A *  5/2000    Bohr et al. ............... 435/173.1
6,331,290 B1 * 12/2001   Morgan ..................... 424/46

FOREIGN PATENT DOCUMENTS

EP    0141768    5/1985
WO    01/89675   11/2001

OTHER PUBLICATIONS

Rediske et al., Ultrasonic Enhancement of Antibiotic Action on *Escherichia coli* Biofilms: an In Vivo Model, Antimicrobial Agents and Chemotherapy, 1999, vol. 43, pp. 1211-1214.*
Derwent Publications Ltd., XP-002262035, AN 1997-490629, Abstract CN1122339.
V. Nornstein et al, "Changes of Surface Tension of Human Serum Albumin Induced by Ultrasonic Cavitation and by pH-Lowering," Studia Biophysica, vol. 125, 1988, No. 3, pp. 179-186.

* cited by examiner

Primary Examiner—Robert A. Wax
(74) Attorney, Agent, or Firm—William H. Holt

(57) ABSTRACT

Proteins may be made by genetically engineered microorganisms, the protein being stored in the form of inclusion bodies (IB). The proteins in the inclusion bodies are in an insoluble and inactive form. They may be dissolved using a solubilization reagent (18), and the resulting solution diluted so that the proteins refold into the active form. This refolding of the protein is enhanced by subjecting a solution or suspension of the protein to low intensity sound waves (25), at a low enough intensity that the protein is not denatured. The intensity may be between 10 and 100 mW/cm$^2$.

7 Claims, 1 Drawing Sheet

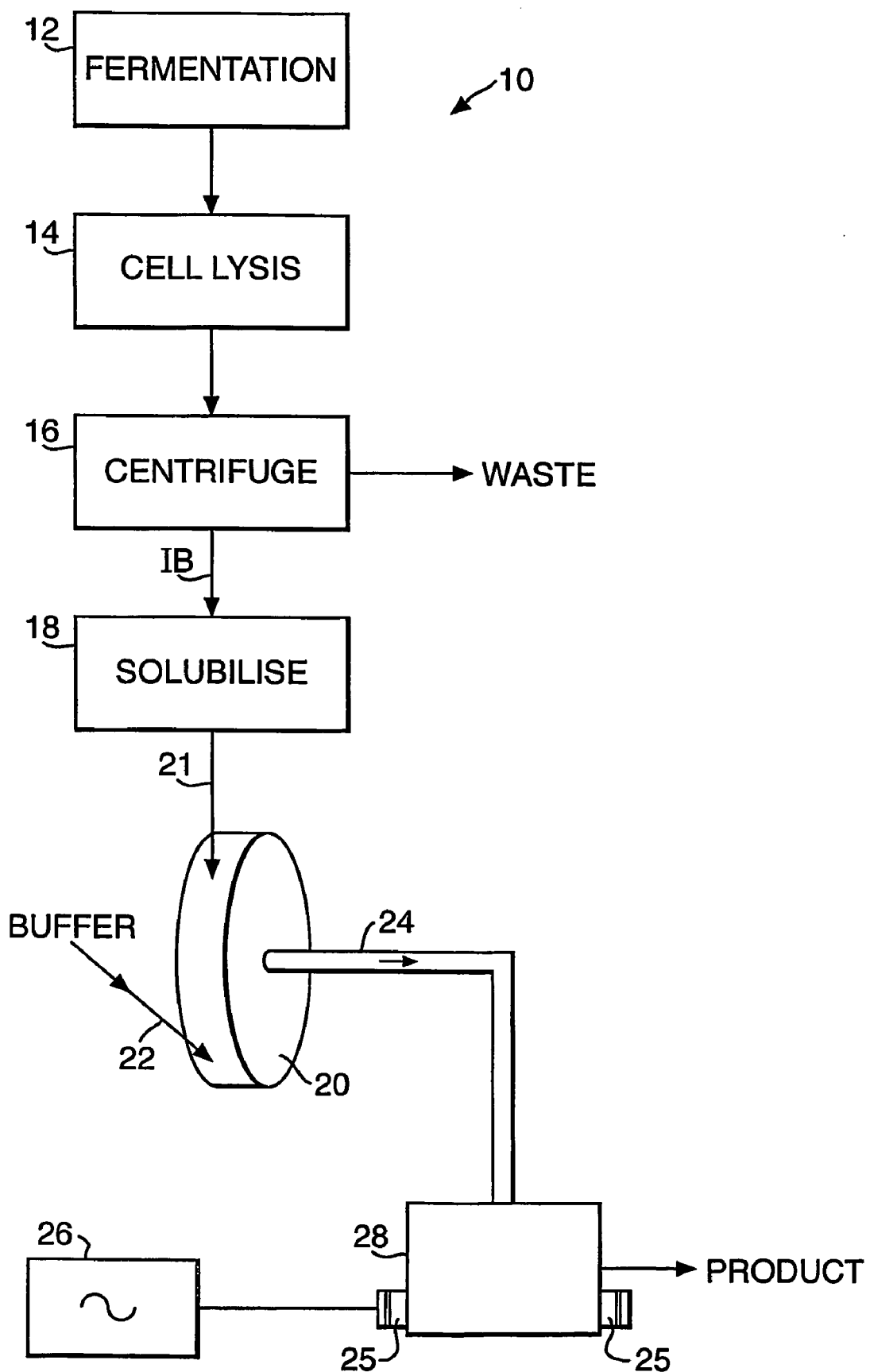

PROTEIN PRODUCTION

This invention relates to a method and an apparatus for obtaining solutions of proteins that are in their correctly folded state, with the correct or active secondary or tertiary structure.

A range of complex organic molecules can be synthesized within cells including bacterial, plant, fungal and mammalian cells. For example this synthesis may be carried out with bacterial cells in a fermentation process. The desired product molecules must then be recovered and purified from the cells. In particular, in the production of proteins from genetically engineered microorganisms, the cells may over-express the protein and create insoluble aggregates of the protein known as inclusion bodies. In a known process these inclusion bodies are isolated from other cell components by cell lysis, followed by for example centrifugation or microfiltration. The proteins in the inclusion bodies are in an insoluble and inactive form, presumably because the molecules are tangled and/or incorrectly folded. A known process involves treating the inclusion bodies with a solubilisation reagent (so the molecules are no longer entangled), and then removing or diluting the solubilisation reagent so that the proteins refold into the active form. This dilution step tends to be inefficient, so that some of the protein reaggregates into an insoluble and inactive form, while the dilution required is usually very high, resulting in the formation of a large volume of very dilute protein solution. On an industrial scale the proportion of protein from the inclusion bodies that is converted into the active product is typically only about 10%, and 20% conversion would be considered very good.

According to the present invention there is provided a method for bringing about refolding of a protein wherein a solution or suspension of the protein is subjected to low intensity sound waves, at a low enough intensity that the protein is not denatured.

The sound waves may be of any convenient frequency, and may be above say 10 or 20 kHz, so the waves are ultrasonic. Typically the frequency is below 1 MHz, and usually below 200 kHz. The intensity must be less than that at which sonocavitation occurs. For example an intensity less than about 0.3 W/cm$^2$, for example 0.05 or 0.1 W/cm$^2$, may be appropriate, although the upper limit for intensity depends upon the geometry of the vessel, the frequency of the sound waves, and the viscosity of the liquid. It also depends on whether or not the liquid contains dissolved gases. It increases with frequency, though not linearly; for example for aerated water at room temperature the threshold increases from about 0.24 W/cm$^2$ at 10 kHz and 0.3 W/cm$^2$ at 20 kHz to about 1.0 W/cm$^2$ at 100 kHz. The values of power given here are those of the electrical power delivered to the transducers, as this is relatively easy to determine.

The solution or suspension of the protein may be produced in any suitable manner. One method involves diluting a solution of solubilised proteins by mixing it with a dilution liquid. This mixing is preferably performed by passage through a fluidic vortex mixer, as this can achieve very rapid and thorough mixing. The irradiation with sound waves may take place immediately after this mixing step.

A fluidic vortex mixer comprises a substantially cylindrical chamber with an axial outlet duct at the centre of an end wall of the chamber, and with at least one substantially tangential inlet near the periphery of the chamber to create a spiralling flow in the chamber. A second liquid is supplied through a second tangential inlet, or through a radial inlet. The chamber contains no turbulence-generating vanes or baffles. Such a mixer achieves a very intimate mixing of the two liquids in a very short time, but does not subject the liquid to high shear. It is also much less prone to being fouled, for example by proteinaceous deposits, than other types of mixer. The residence time, that is the time taken by the mixture to pass through the mixer, can be less than 1 s.

Examples of proteins that may be refolded in this way include those intended for therapeutic purposes, and those from genetically engineered cell lines, such as interferons, protein vaccines, enzymes and hormones, and the term protein should also be construed as encompasssing glycoproteins and lipoproteins. It will also be appreciated that the process of the invention may be applied to a mixture of different proteins.

The invention also provides an apparatus for refolding proteins.

The invention will now be further and more particularly described, by way of example only, and with reference to the accompanying drawing which shows a flow diagram for a protein recovery system.

Referring to the drawing, a procedure 10 is illustrated for obtaining active protein. Bacteria (*Escherichia coli*) genetically engineered to make the desired protein are grown 12 in a fermentation vessel. The bacteria over-express the protein, which is stored in inclusion bodies within the bacteria in an insoluble, tangled and inactive state. When sufficient fermentation has taken place, the aqueous suspension of the cells is subjected to cell lysis 14 and then centrifugation 16 to separate the inclusion bodies IB from a waste stream. The inclusion bodies IB are then solubilised 18 by dissolution in a suitable reagent such as urea or guanidine hydrochloride, this causing the proteins to become disentangled.

The resulting solution of inactive proteins is supplied to one tangential inlet 21 of a fluidic vortex mixer 20, and refolding buffer as a diluting agent is supplied to a second tangential inlet 22 of the mixer 20, so that a dilute solution emerges from an axial outlet 24 after a residence time in the mixer 20 typically less than 0.1 s. The refolding buffer may be an aqueous solution containing the solubilising agent at a lower concentration, and also compounds such as glutathione to assist the refolding process. The flow rate of the refolding buffer may be 200 times greater than that of the solution of inactive proteins. By way of example, the cylindrical chamber in the mixer 20 might be of diameter 10 mm and of height 2 mm, each inlet duct 21 and 22 being of cross-sectional area 1 mm$^2$, and the outlet duct 24 being of cross-sectional area 2 mm$^2$; with a flow rate of 1 liter per minute the residence time would be about 8 ms. If the flow rate through this mixer 20 were halved to 0.5 l/min the mean residence time would double to about 16 ms.

The outflow from the mixer 20 flows through the outlet duct 24 into a holding tank 28 to allow time for the protein to refold into the active form. One or more ultrasonic transducers 25 are coupled to the wall of the tank 28, connected to a signal generator 26. The transducers 25 are driven at a frequency typically in the range 10 kHz to 250 kHz, and for example may be driven at 130 kHz. In this case each transducer 25 is arranged to generate a maximum intensity of 0.6 W/cm$^2$ in the liquid phase (which is below the cavitation threshold at this frequency) so the contents are subjected to low intensity ultrasound. The holding tank 28 can be a plug flow reactor, or a stirred reaction vessel with baffles; the plug flow reactor can be of the pulsed type, for example as described in WO 00/29545, and may be operated in a batch or continuous mode. The residence time in the holding tank 28 is desirably in the range 1 hour to 10 hours, and preferably between 2 hours and 6 hours.

Ultrasonic transducers may also be arranged to subject the contents of the outlet duct 24 to such low intensity ultrasonic waves. In any event, whether the solution is subjected to sound waves while flowing in the outlet duct 24 or being held in the tank 28, it is important that the intensity is not so high that cavitation events (which could cause denaturing of the protein) occur. Hence the intensity should be less than 300 mW/cm$^2$ and usually less than 100 mW/cm$^2$; but the intensity must be high enough to deposit a significant amount of energy, so it should be more than 10 mW/cm$^2$. Furthermore the transducers may be energised at a fixed frequency, such as 20 or 40 kHz, or alternatively the frequency may vary for example between 19.5 and 20.5 kHz.

The solution may also be subjected to further processing such as liquid chromatography and filtration to separate any agglomerated (and therefore inactive) protein from the active protein in solution.

The invention claimed is:

1. A method for bringing about refolding of a protein wherein a solution or suspension of the protein is subjected to low intensity sound waves at a frequency above 10 kHz and below 1 MHz, at a low enough intensity that the protein is not denatured, the intensity being less than that at which sonocavitation occurs.

2. A method as claimed in claim 1 wherein the sound wave intensity is between 10 and 300 mW/cm$^2$.

3. A method as claimed in claim 1 wherein the intensity is less than 100 and mW/cm$^2$ .

4. A method as claimed in claim 1 wherein the solution or suspension of the protein is produced by diluting a solution of solubilised proteins by mixing it with a dilution liquid.

5. A method as claimed in claim 4 wherein the mixing is performed by passage through a fluidic vortex mixer.

6. A method as claimed in claim 2 wherein the solution or suspension of the protein is produced by diluting a solution of solubilised proteins by mixing it with a dilution liquid.

7. A method as claimed in claim 3 wherein the solution or suspension of the protein is produced by diluting a solution of solubilised proteins by mixing it with a dilution liquid.

* * * * *

UNITED STATES PATENT AND TRADEMARK OFFICE
CERTIFICATE OF CORRECTION

PATENT NO.         : 7,183,378 B2  
APPLICATION NO. : 10/528406  
DATED                 : February 27, 2007  
INVENTOR(S)        : Linda Jane McCausland Page 1 of 1

It is certified that error appears in the above-identified patent and that said Letters Patent is hereby corrected as shown below:

On Title Page  
On page 1, column 1, the following is added to  
Item (30) Foreign Application Priority Data:

Sep. 18, 2002  PCT/GB02/04223

Signed and Sealed this

Eighth Day of May, 2007

JON W. DUDAS  
*Director of the United States Patent and Trademark Office*